US011324841B2

(12) United States Patent
Lee et al.

(10) Patent No.: US 11,324,841 B2
(45) Date of Patent: *May 10, 2022

(54) METAL OXIDE NANOPARTICLE-BASED MAGNETIC RESONANCE IMAGING CONTRAST AGENT WITH A CENTRAL CAVITY

(71) Applicant: INTRON BIOTECHNOLOGY, INC., Gyeonggi-do (KR)

(72) Inventors: Kwang Yeol Lee, Gyeonggi-do (KR); Min Sik Kim, Seoul (KR); Taek Hoon Kim, Seoul (KR); Ngoc Phan Vu, Hanoi (VN)

(73) Assignee: INTRON BIOTECHNOLOGY, INC., Gyeonggi-do (KR)

( * ) Notice: Subject to any disclaimer, the term of this patent is extended or adjusted under 35 U.S.C. 154(b) by 0 days.

This patent is subject to a terminal disclaimer.

(21) Appl. No.: 16/943,326

(22) Filed: Jul. 30, 2020

(65) Prior Publication Data

US 2021/0008228 A1 Jan. 14, 2021

Related U.S. Application Data

(62) Division of application No. 14/782,552, filed as application No. PCT/KR2013/002847 on Apr. 5, 2013, now abandoned.

(51) Int. Cl.
| | | |
|---|---|---|
| *A61K 49/18* | (2006.01) | |
| *B01J 20/06* | (2006.01) | |
| *B01J 20/28* | (2006.01) | |
| *B01J 23/889* | (2006.01) | |
| *B01J 35/00* | (2006.01) | |
| *H01M 4/36* | (2006.01) | |
| *H01M 4/50* | (2010.01) | |
| *H01M 4/52* | (2010.01) | |
| *H01M 4/86* | (2006.01) | |
| *H01M 4/90* | (2006.01) | |

(52) U.S. Cl.
CPC ........ *A61K 49/186* (2013.01); *A61K 49/1818* (2013.01); *A61K 49/1875* (2013.01); *B01J 20/06* (2013.01); *B01J 20/28016* (2013.01); *B01J 23/8892* (2013.01); *B01J 35/0013* (2013.01); *H01M 4/364* (2013.01); *H01M 4/50* (2013.01); *H01M 4/52* (2013.01); *H01M 4/8652* (2013.01); *H01M 4/9016* (2013.01)

(58) Field of Classification Search
CPC ... A61K 49/186; A61K 49/1818; B01J 20/06; B01J 20/28016; B01J 23/8892; B01J 35/0013; H01M 4/8652; H01M 4/9016; H01M 4/364; H01M 4/50; H01M 4/52
See application file for complete search history.

(56) References Cited

U.S. PATENT DOCUMENTS

| 2009/0297441 A1 | 12/2009 | Canham et al. |
| 2011/0165086 A1 | 7/2011 | Lee et al. |
| 2011/0311635 A1 | 12/2011 | Stucky et al. |
| 2013/0023714 A1 | 1/2013 | Johnson et al. |

FOREIGN PATENT DOCUMENTS

| WO | WO 2009/055090 A1 | 4/2009 |
| WO | WO 2011/151631 A1 | 12/2011 |

OTHER PUBLICATIONS

Zhang et al., Solid State Sciences, 2009, 11, p. 1265-1269. (Year: 2009).*
Nano Today (2010) 5, 183-196 "Recent advances in syntheses and therapeutic applications of multifunctional porous hollow nanoparticles", Kai Cheng. Shouheng Sun, Department of Chemistry, Brown University, 324 Brook Street, Providence, RI 02912, USA, received in revised from Apr. 4, 2010; accepted Apr. 6, 2010 Available online May 1, 2010.
Kai Cheng "Porous Hollow $Fe_3O_4$ Nanoparticles for Targeted Delivery and Controlled Release of Cisplatin." Department of Chemistry, Brown University, Providence, Rhode Island 02912; J.AM. Chem. SOC. 2009, 131, 10637-10644.
Teyeb Ould-Ely "Manganese (II) Oxide Nanohexapods: Insight into Controlling the Form of Nanocrystals". Department of Chemistry, MS 60, Center for Biology and Environmental Nanotechnology, Department of Chemical and Biomolecular Engineering, MS362, and Department of Earth Science, MS 126, Rice University, University of Houston, Texas 77204-5931—XP-002762951-10.1021/cm052492 © 2006 American Chemical Society Published on Web Mar. 7, 2006.
Yuanzhe Piao "Wrap-bake-peel Process for Nanostructural Transformation from β-FeOOH Nanorods to Biocompatible Iron Oxide Nanoapsules". National Creative Research Initiative Center for Oxide Nanocrstalline Materials and School of Chemical and Biological Engineering, Seoul National University, Seoul 151-744 South Korea.
Jongmin Shin et al., "Hollow Manganese Oxide Nanoparticles as Multifunctional Agents for Magnetic Resonance Imaging and Drug Delivery", XP-002762948, Angew. Chem. Int. Ed. 2009, 48, 321-324 © 200* Wiley-VCH Verlag GmbH & Co. LGaA, Weinheim, DOI: 10.1002/anie. 200802323.

(Continued)

*Primary Examiner* — Michael G. Hartley
*Assistant Examiner* — Leah H Schlientz
(74) *Attorney, Agent, or Firm* — von Briesen & Roper, s.c.

(57) ABSTRACT

The present invention relates to a magnetic resonance imaging (MRI) contrast agent, particularly an MRI contrast agent derived from nanoparticle that is porous first metal-doped second metal oxide nanoparticle with a central cavity, and a method for producing the same. The MEI contrast agent made in accordance with the present invention can be used not only as a drug-delivery agent for therapy but also as an MRI contrast agent for diagnosis.

8 Claims, 8 Drawing Sheets

(56) References Cited

OTHER PUBLICATIONS

Taekhoon Kim et al., "Urchin-Shaped Manganese Oxide Nanoparticles as pH-Responsive Activatable $T_1$ Contrast agents for Magnetic Resonance Imaging", XP002762949, Angew. Chem Int. Ed 2011, 50, 10589-10593 © 2011 Wiley-VCH Verlag GmbH & Co. KGaA, Weinheim DOI: 10.1002/anie.201103108.
International Search Report Application No. PCT/KR2013/002847H dated Dec. 30, 2013.
Cheng, K. et al. "Recent advances in syntheses and therapeutic applications of multifunctional porous hollow nanoparticles"; Nano Today, 2010, vol. 5, pp. 183-1966 see pp. 183-185, 187-188, 194.

* cited by examiner

METAL OXIDE NANOPARTICLE-BASED MAGNETIC RESONANCE IMAGING CONTRAST AGENT WITH A CENTRAL CAVITY

CROSS-REFERENCE TO RELATED APPLICATION

This application is a divisional under 35 U.S.C § 121 of U.S. non-provisional patent application Ser. No. 14/782,552, filed on Oct. 5 2015, which vas a U.S. national phase filing under 35 USC § 371 of International Patent Application No. PCT/KR2013/002846 filed on Apr. 5, 2013.

TECHNICAL FIELD

The present invention relates to a magnetic resonance imaging (MRI) contrast agent, particularly a metal oxide nanoparticle-based MRI contrast agent that can be used not only as a drug-delivery agent but also as an MRI contrast agent, wherein the nanoparticle is porous metal oxide nanoparticle with a central cavity.

BACKGROUND ART

Among various molecular imaging techniques, magnetic resonance imaging (MRI) is one of the most powerful and non-invasive diagnostic tools because MRI can provide image with excellent anatomical details based on the interaction of protons with the surrounding molecules of tissues.

MRI contrast agents are a group of contrast media used to improve the visibility of internal body structures by increasing contrast between normal tissues and abnormal tissues in MRI. MRI contrast agents alter the T1 (longitudinal) and T2 (transverse) relaxation times of tissues and body cavities where they are present. Depending on the image weighting, this can give a higher or lower signal. Most MRI Contrast agents work through shortening the relaxation time of protons located nearby.

MRI contrast agent is defined by the two-principle nuclear magnetic resonance processes of spin relaxation, T1 (longitudinal), and T2 (transverse) (Journal of Nuclear Cardiology 11(6): 733-743, 2004).

Paramagnetic metal ions used as T1 MRI contrast agents principally accelerate T1 relaxation and produce the "bright" contrast in a T1-weighted image, whereas superparamagnetic metal oxides used as T2 MRI contrast agents primarily increase the rate of T2 relaxation and create "dark" contrast effects.

Multifunctional MRI contrast agents capable of being used in drug delivery have been received considerable attention as attractive MRI contrast agents for diagnosis and therapy. In this case, the process of delivery and release of drug can be monitored in real-time by MRI. Therefore, intensive attempts are required to develop multifunctional MRI contrast agents that can be used in drug delivery as well as MRI.

As the said multifunctional MRI contrast agents, several types of inorganic nanoparticles with cavity structures have been developed as theranostic nanoplatforms (Nat. Mater. 7: 242, 2008; Angew, Chem. Int. Ed. 48: 321, 2009; J. Am. Chem. Soc. 131: 10637, 2009; ACS Nano 4: 6001, 2010; Nat. Mater. 8: 935, 2009). For effective loading and release of drugs with the said multifunctional MRI contrast agents with cavity structures, fine control of the physical dimensions and morphology of the cavity structures of nanoparticles for MRI contrast agents is highly desirable because the drug loading efficiency of nanoparticles is determined by the physical dimensions and morphology of the cavity structures of nanoparticles, as well as the nature of the drug-cavity interaction. Until now, effective method for fine control of the physical dimensions and morphology of the cavity structures of nanoparticles for MRI contrast agents is not available due to its difficulty.

Numbers of papers and patent descriptions have been cited in this description and the citation is marked in parentheses. The descriptions of cited papers and patent documents are attached in this invention so that the art and text of this invention can be more clearly understood.

DISCLOSURE

Technical Problem

It is an object of the present invention to overcome the problems of the prior art and thus to develop a technique and method long requested.

Precisely, it is an object of the present invention to provide a nanoparticle-based MRI contrast agent that can be used not only as a drug-delivery agent but also as an MRI contrast agent, wherein the nanoparticle is porous metal oxide nanoparticle with a central cavity.

It is another object of the present invention to provide a method for producing a nanoparticle-based MRI contrast agent that can be used not only as a drug-delivery agent but also as an MRI contrast agent, wherein the nanoparticle is porous metal oxide nanoparticle with a central cavity.

Technical Solution

To provide multifunctional MRI contrast agents capable of being used in drug delivery, the present inventors developed method to generate MRI contrast agents derived from porous first metal-doped second metal oxide nanoparticles with a central cavity by synthesizing first metal oxide nanoparticles under inert gas environment, forming an epitaxial layer of second metal oxide on the surface of first metal oxide nanoparticles under inert gas environment, maintaining the formation of the layer of second metal oxide under dry air environment, removing the first metal oxide phase by treatment with acidic liquid at high temperature to form first metal oxide-doped second metal oxide nanoparticles having a central cavity, and coating the nanoparticles with a biocompatible polymer, and then completed this invention by confirming that the nanoparticle-based MRI contrast agent could be used as multifunctional MRI contrast agents capable of being used in drug delivery and MRI.

So, the present invention provides an MRI contrast agent derived from nanoparticle that is porous first metal-doped second metal oxide nanoparticle with a central cavity, and a method for producing the same. A sectional view illustrating one exemplary type of MRI contrast agent of the present invention is presented in FIG. 1.

In a preferred embodiment of the present invention, manganese oxide was selected as first metal oxide, but not limited thereto and other metal oxides such as cobalt (II) oxide and zinc (II) oxide can also be selected.

In a preferred embodiment of the present invention, iron oxide is selected as second metal oxide forming an epitaxial layer on the surface of first metal oxide nanoparticles, but not limited thereto and other paramagnetic or superparamagnetic metal oxides can also be selected, which are exemplified by chromium (III) oxide, gadolinium (III) oxide, cobalt (II) oxide and nickel (II) oxide, but not limited thereto.

The drug loading efficiency of the MRI contrast agent of the present invention is determined by the physical dimensions and morphology of the cavity of nanoparticles, as well as the nature of the drug-cavity interaction. For effective encapsulation and release of drugs, fine control of the physical dimensions and morphology of the cavity of oxide nanoparticle is crucial. The present invention can provide a method to control these features of the MRI contrast agents by controlling the physical dimensions and morphology of template cores (i.e., first metal oxide nanoparticles). These factors of template cores can be controlled by adjusting the amount of surfactant, reaction time, and reaction temperature. In addition, any shape of template cores can be selected for the present invention, which are exemplified by octahedral, cross-shaped, urchin-shaped, and cubic nanoparticles, but not limited thereto.

Various polymers can be used as a biocompatible polymer used in coating the nanoparticle with it. Preferred examples of the biocompatible polymers include biopolymers such as chitosan, elastin, hyaluronic acid, alginate, gelatin, collagen, and cellulose; and synthetic polymers such as polyethylene glycol (PEG), polyethylene oxide (PEO), polycaprolactone (PCL), polylactic acid (PLA), polyglycolic acid (PGA), poly(lactic-co-glycolic) acid (PLGA), poly(3-hydroxybutyrate-co-3-hydroxyvalerate) (PHBV), polydioxanone (PDO), poly(L-lactide-co-caprolactone), poly (ester urethane) (PEU), poly(L-lactide-co-D-lactide), poly (ethylene-co-vinyl alcohol), poly (acrylic acid) (PAA), poly (vinyl alcohol) (PVA), polyvinylpyrrolidone (PVP), polystyrene (PS) and polyaniline (PAN), but not limited thereto.

The said biocompatible polymers can be modified for improving biocompatibility and stability of MRI contrast agent. The methods useful for modification of polymer have been well-known and well-performed by those in the art, which means these methods are very general and thus no further explanation is necessary.

The said biocompatible polymers can be further modified by conjugation with various useful moieties such as targeting moieties or diagnostic moieties. The said targeting moieties include antibodies, antibody fragments, aptamers, and various ligands binding to receptors displayed on the surface of target cell, but not limited thereto. And the said diagnostic moieties include diagnostic imaging moieties such as fluorophores, optical reporters and quantum dots; computed tomography (CT) probes such as iodine-based compounds and gold nanoparticles; and nonmetallic radioisotopes such as indium (In), technetium (Tc) and fluorine (F), but not limited thereto. The methods for conjugation of polymers and useful moieties have been well-known and well-performed by those in the art, which means these methods are very general and thus no further explanation is necessary.

In a preferred embodiment of the present invention, doxorubicin was selected as a model drug loaded in MRI contrast agents of the present invention, but not limited thereto and other various drugs can also be selected, which are exemplified by anticancer drugs such as taxol, paclitaxel and docetaxel; and antibiotics such as novobiocin, erythromycin, macrolide antibiotics and bacteriophage endolysin; but not limited thereto.

The MRI contrast agents of the present invention can be prepared by dispersion of the MRI contrast agent particles in pharmaceutically acceptable liquid media. The methods for preparation of pharmaceutically acceptable MRI contrast agent injectable composition have been well-known and well-performed by those in the art, which means these methods are very general and thus no further explanation is necessary.

The present invention also provides a method for producing an MRI contrast agent derived from nanoparticle that is porous first metal-doped second metal oxide nanoparticle with a central cavity, which comprises the following steps:

A) synthesizing first metal oxide nanoparticles under inert gas environment;

B) forming an epitaxial layer of second metal oxide on the surface of first metal oxide nanoparticles under inert gas environment;

C) maintaining the formation of the layer of second metal oxide under dry air environment;

D) removing the first metal oxide phase by treatment with acidic liquid at high temperature to form first metal oxide-doped second metal oxide nanoparticles having a central cavity; and E) coating the nanoparticles with a biocompatible polymer.

In a preferred embodiment of the present invention, thermal decomposition of metal precursors is utilized in synthesis of first and second metal oxides, but not limited thereto and other methods such as precipitation, gas evaporation method, mixed gas method, spray drying and mechanical alloying can also be used.

A variety of metal salts can be utilized as metal precursors, which are exemplified by metal acetate, metal acetylacetonate, metal bromide, metal carbonate, metal chloride, metal fluoride, metal iodide, metal nitrate, metal sulfate, metal oleate, metal formate, their hydrate forms, and mixture of the said metal salts, but not limited thereto.

As surfactants used in thermal decomposition of metal precursors, alkyl carboxylic acids such as oleic acid, lauric acid, stearic acid, mysteric acid and hexadecanoic acid; alkyl amines such as oleylamine, laurylamine, hexadecylamine, trioctylamine and dioctylamine; and mixture of alkyl carboxylic acids or alkylamines can be used, but not limited thereto. As alkylamines, primary alkylamines such as oleylamine, laurylamine, hexadecylamine are more preferred.

As organic solvents used in thermal decomposition of metal precursors, organic solvents that have higher boiling point than the temperature of thermal decomposition reaction are preferred. Hydrocarbon compounds such as alkanes, alkenes, alkynes, cycloalkanes and alkadiens; ether compounds such as butyl ether, hexyl ether, octyl ether and decyl ether; heterocyclic compounds such as pyridine and tetrahydrofuran; aromatic compounds such as toluene, xylene, mesitylene and benzene; and amine compounds such as trioctylamine and oleylamine are exemplified, but not limited thereto.

As acidic liquid used in facet-etching of first metal oxide and removing the first metal oxide phase, various organic acids such as oleic acid and palmitic acid; and various acidic buffers can be used, but not limited thereto. As acidic liquid, oleic acid is more preferred.

The exposure of first metal oxide nanoparticles to air during formation of a layer of second metal oxide on the surface of first metal oxide nanoparticles under dry air environment forms a thin layer of first metal oxide with higher oxidation state. For example, in the presence of oxygen, the surface of MnO nanoparticles is partially converted to a $Mn_3O_4$ phase. This oxidation not homogeneous, leading to formation of multiple domains of the first metal oxide with higher oxidation state on the surface of the first metal oxide nanoparticles. The presence of the patches of the higher oxidation state form of first metal oxide on the surface of first metal oxide nanoparticles is crucial to generate the porous second metal oxide shell. Due to the existence of the pores in second metal oxide shell, the access of acidic liquid to etch out the first metal oxide core is possible. When the first metal oxide nanoparticles are directly coated with a second metal oxide layer by decomposition of precursor of second metal oxide under inert gas environment, second metal oxide without pore structure is synthesized. The second metal oxide without pore structure does not permit the access of acidic liquid to etch out the first metal oxide core. In addition, the first metal ion within the higher oxidation state form of first metal oxide diffuses out to the newly formed second metal oxide shell during formation of an epitaxial layer of second metal oxide on the surface of first metal oxide nanoparticles. The higher oxidation state form of first metal oxide is readily mixed with the newly formed second metal oxide phase to form a first metal-doped second metal oxide phase. As a result, the first metal-doped second metal oxide nanoparticles can be synthesized. In some cases, this phenomenon can provide additional merits such as improvement of image contrast enhancement or functionality as T1-T2 dual mode MRI contrast agents.

Consequently, performance of the reaction to form the layer of second metal oxide under dry air condition is very important.

The porous metal oxide nanoparticles with a central cavity made in accordance with the present invention can be used in various applications apart from using as MRI contrast agents, which are exemplified by adsorbent nanoparticles applicable in removal of toxic heavy metal ions such as mercury ions, lead ions, cadmium ions, chrominium ions; catalyst supports or catalysts; electrodes; and battery components, but not limited thereto.

Advantageous Effect

The present invention can provide a method for producing an MRI contrast agent derived from nanoparticle that is porous first metal-doped second metal oxide nanoparticle with a central cavity. The MRI contrast agent made in accordance with the present invention can be used not only as a drug-delivery agent for therapy but also as an MRI contrast agent for diagnosis. The MRI contrast agents loaded with drugs can enhance the therapeutic effect by real-time monitoring of the entire process of drug delivery and drug release as well as therapeutic response. According to the methods of the present invention, control of surface nature, physical dimensions and morphology of the cavity of MRI contrast agents can be possible; thus, control of the loading and release efficiencies of drugs can also be possible.

DESCRIPTION OF DRAWINGS

The application of the preferred embodiments of the present invention is best understood with reference to the accompanying drawings, wherein.

MODE FOR INVENTION

As explained hereinbefore, the present invention is to provide an MRI contrast agent derived from nanoparticle that is porous first metal-doped second metal oxide nanoparticle with a central cavity, which can be used not only as a drug-delivery agent but also as an MRI contrast agent, and a method for producing the same.

Practical and presently preferred embodiments of the present invention are illustrative as shown in the following Examples.

However, it will be appreciated that those skilled in the art, on consideration of this disclosure, may make modifications and improvements within the spirit and scope of the present invention.

Figure 1:
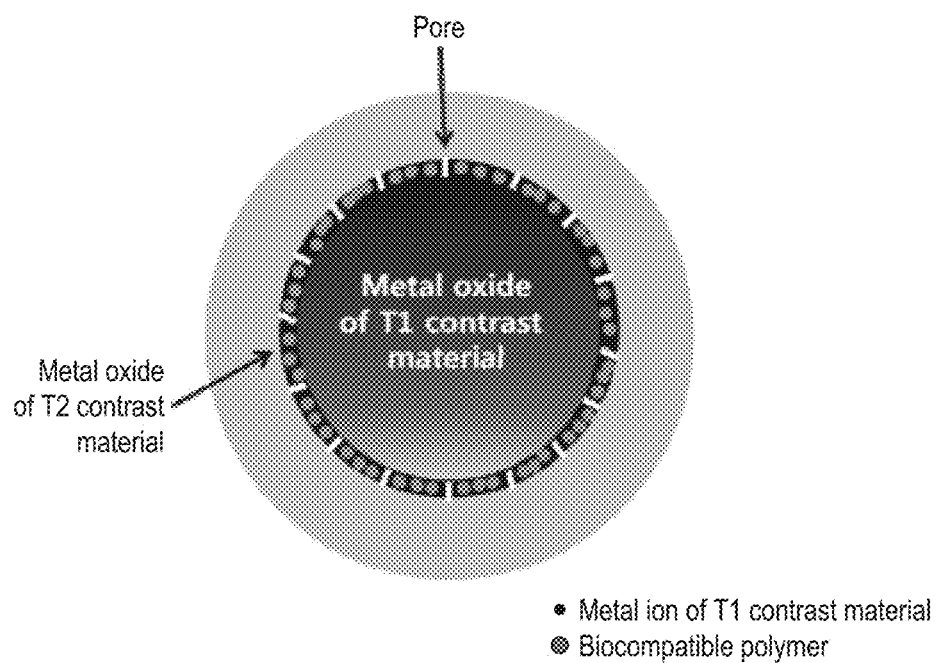
FIG. 1 is a sectional view illustrating one exemplary type of MRI contrast agent of the present invention.
Figure 2:
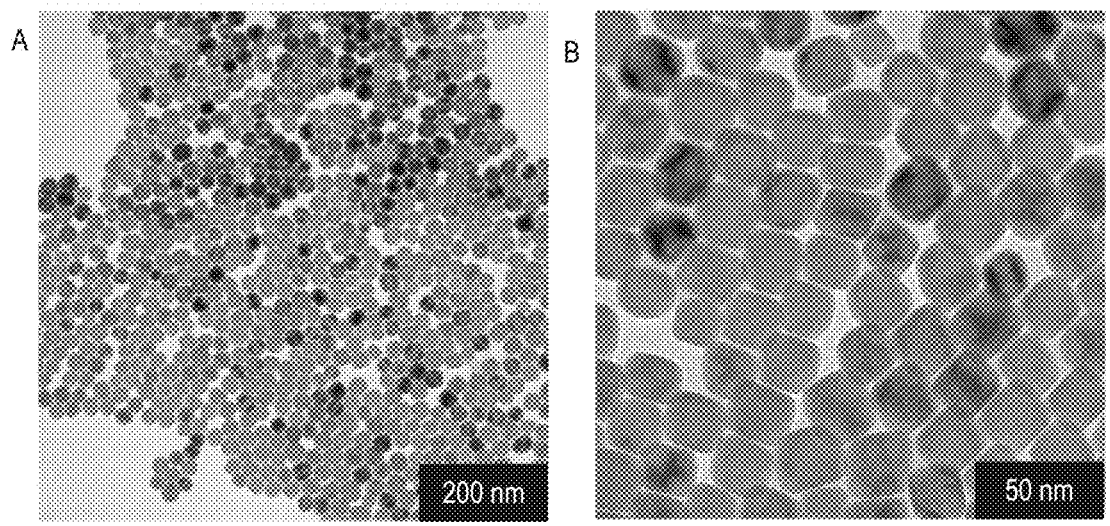
FIG. 2 is a transmission electron microscopy (TEM) image of octahedral manganese (II) oxide (MnO) nanoparticles (a) Low magnification, and (b) high magnification.
Figure 3:
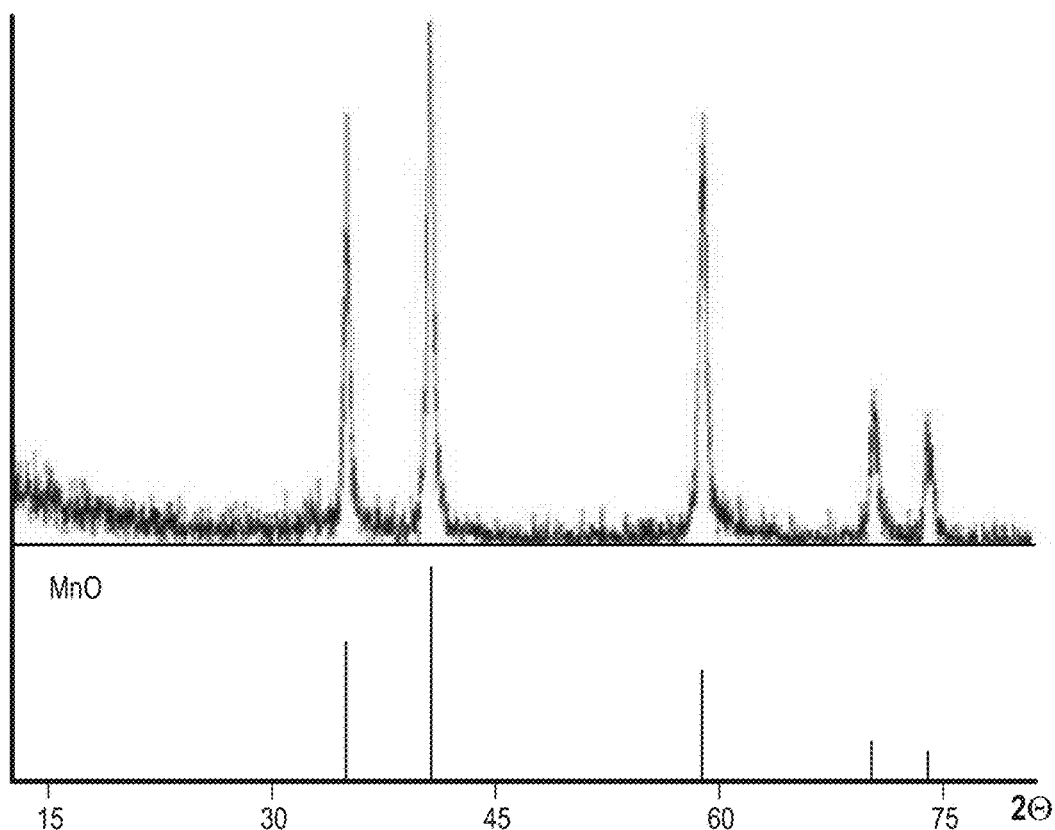
FIG. 3 is an X-ray diffraction (XRD) pattern of octahedral MnO nanoparticles as synthesized.

Example 1: Preparation of Manganese (II) Oxide Nanoparticles with Various Shapes <1-1> Preparation of Octahedral Manganese Oxide Nanoparticles The octahedral manganese (II) oxide nanoparticles were synthesized by using the method reported (Chem. Mater. 18: 1821, 2006) with some modifications. Briefly, manganese (II) formate ($Mn(HCOO)_2$, 5 mmol), oleic acid (13 mmol) and trioctylamine (15 mmol) were mixed in a 50 ml round-bottom flask. The mixture was heated in an oil bath to 120° C. with a magnetic stirring and kept at that temperature for 3 hours under a strong flow of argon gas. Then the temperature was increased to 330° C. with the heating rate of 30° C. per minute and the reaction was kept at that temperature until the green color appeared. The green solids were obtained by cooling the reaction solution down to room temperature and were washed with 1-propanol followed by a centrifugation (3 min, 3,500 rpm). The collected solids were washed again with ethyl alcohol several times before drying overnight in an oven. The results of TEM and. XRD analysis are presented in FIG. 2 and FIG. 3, respectively.

<1-2> Preparation of Cross-Shaped Manganese Oxide Nanoparticles

Figure 4:
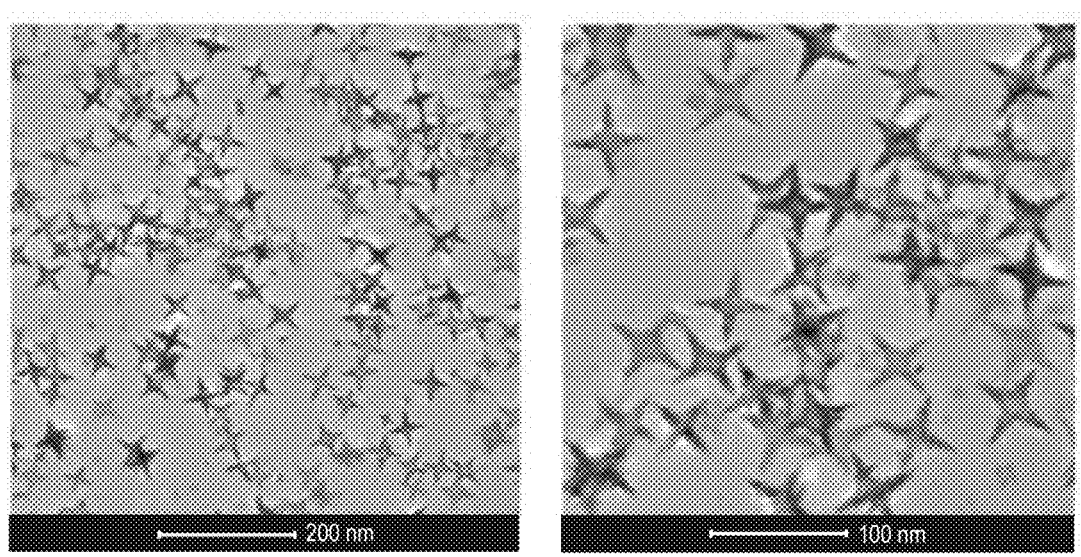
FIG. 4 is a TEM image of cross-shaped MnO nanoparticles.

Manganese (II) acetate (1.4 mmol), oleylamine (3.0 mmol), oleic acid (1.5 mmol) and trioctylamine (6.2 ml) were loaded into a 100 ml Schlenk tube. The Schlenk tube was heated in an oil bath to 270° C. with a heating rate of 18° C. per minute and kept at that temperature for 1 hour with magnetic stirring and argon gas flow. Then oleic acid (2.4 mmol) and trioctylamine (1.24 ml) were injected to the reaction mixture followed by further heating at the temperature of 270° C. for 1 h. The green solids were obtained by cooling the reaction solution down to room temperature and washed with 1-propanol followed by a centrifugation (3 min, 3,500 rpm). The collected solids were washed again with ethyl alcohol several times before drying overnight in an oven. The result of TEM analysis is presented in FIG. 4.

Figure 5:
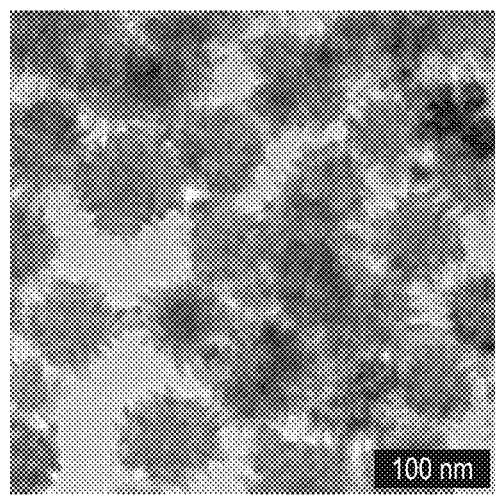
FIG. 5 is TEM image of urchin-shaped MnO nanoparticles.

<1-3> Preparation of Urchin-Shaped Manganese Oxide Nanoparticles 6.2 ml trioctylamine, 1.4 mmol manganese (II) acetate, 3 mmol oleylamine and 1.5 mmol oleic acid were added to 100 ml Schlenk tube. The Schlenk tube was heated to 270° C. at a rate of 18° C./min in an oil bath under nitrogen blanket (the $N_2$ gas was blown at the flow rate of 40 cc/min). After 1 h at 270° C., the formation of large MnO nanoparticles was completed. Then the formed large polycrystalline MnO nanoparticles were subjected to facet-selective etching. Specifically, in order to affect the anisotropic etching, oleic acid (1.6 mmol) and trioctylamine (1.24 ml) was injected to the reaction mixture, and the resulting solution was further heated at 270° C. for 1 h. The reaction mixture was cooled to room temperature, and excess ethanol was added into the solution to give a brown precipitate. The result of TEM analysis is presented in FIG. 5.

<1-4> Preparation of Cubic Manganese Oxide Nanoparticles

Figure 6:
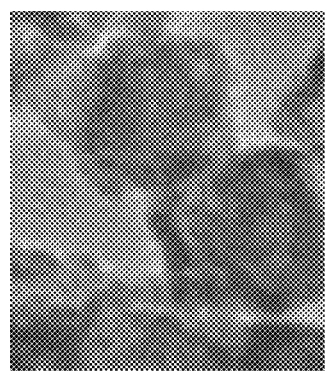
FIG. 6 is a TEM image of cubic MnO nanoparticles.

Manganese (II) acetate (0.4 mmol), sodium oleate (0.4 mmol), oleylamine (3.0 mmol), oleic acid (1.5 mmol) and trioctylamine (6.2 ml) were loaded into a 100 ml Schlenk tube. The Schlenk tube was heated in an oil bath to 270° C. with a heating rate of 18° C. per minute and kept at that temperature for 1 hour with magnetic stirring and argon gas flow. Then oleic acid (2.4 mmol) and trioctylamine (1.24 ml) were injected to the reaction mixture followed by further heating at the temperature of 270° C. for 1 h. The green solids were obtained by cooling the reaction solution down to room temperature and were washed with 1-propanol followed by a centrifugation (3 min, 3,500 rpm). The collected solids were washed again with ethyl alcohol several times before drying overnight in an oven. result of TEM analysis is presented in FIG. 6.

Figure 7:
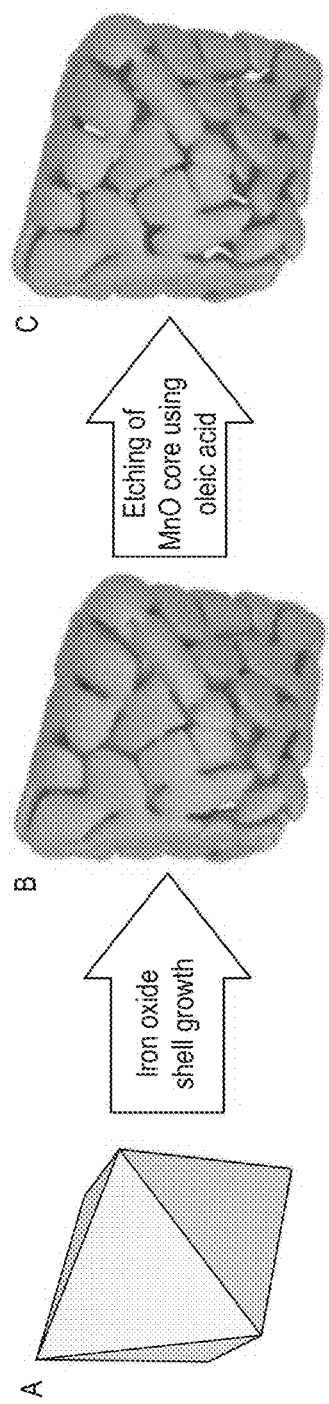
FIG. 7 is a diagram illustrating the synthesis scheme of nanoparticles of the present invention. (a) MnO nanoparticle, (b) Mn-doped iron oxide nanoparticle with MnO core, and (C) Mn-doped iron oxide nanoparticle with a central cavity.
Figure 8:
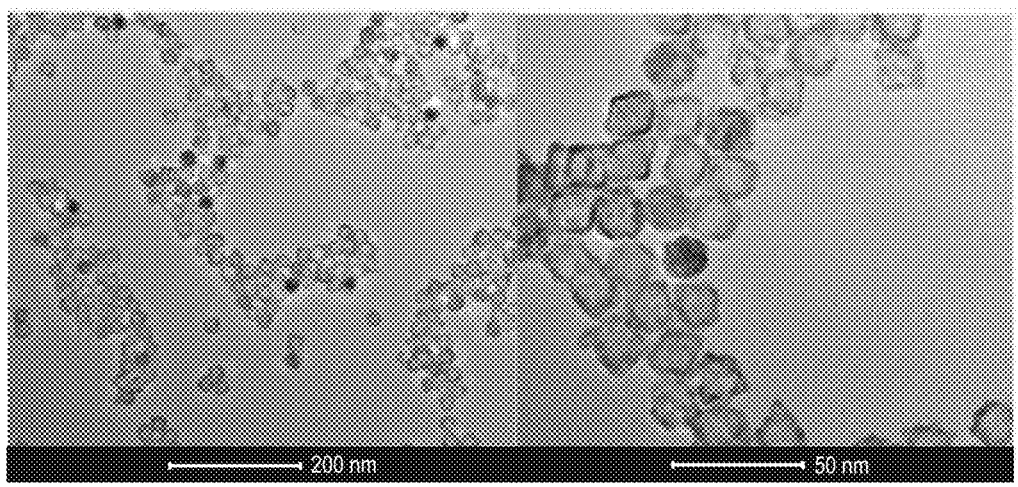
FIG. 8 is a TEM image of the Mn-doped iron oxide nanoparticles with a central cavity derived from octahedral MnO nanoparticles according to the present invention.
Figure 9:
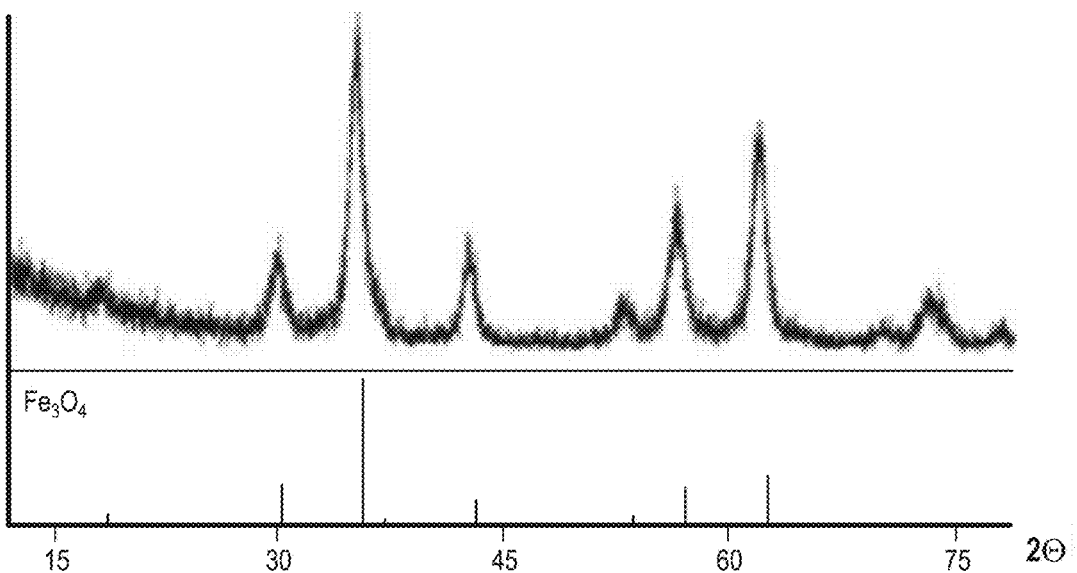
FIG. 9 is an XRD pattern of the Mn-doped iron oxide nanoparticles with a central cavity derived from octahedral MnO nanoparticles according to the present invention.

Example 2: Preparation of Manganese (Mn)-Doped Iron Oxide Nanoparticles with a Central Cavity <2-1> Preparation of Mn-Doped Iron Oxide Nanoparticles with a Central Cavity Using Octahedral Manganese Oxide Nanoparticles 14.2 mg of the octahedral MnO nanoparticles and 0.375 mmol of iron (III) acetylacetonate were added into the solution of oleic acid (0.05 mmol), oleylamine (1 mmol) and trioctylamine (2 ml) in a 100 ml Schlenk tube. The Schlenk tube was heated in the oil bath to 210° C. with the heating rate of 10° C. per min under vigorous stirring and kept at this temperature for 20 min under argon. Then the reaction mixture was heated at 310° C. for 30 min under dry air environment (oxygen percentage is 20%). The black solution was cooled to room temperature, and oleic acid (1.3 mmol) and trioctylamine (0.5 ml) was added to it. Then the reaction mixture was heated to 240° C. and kept at this temperature for 30 min under dry air environment. After cooling down to room temperature, the Mn-doped iron oxide nanoparticles with a central cavity were precipitated with an addition of acetone and n-propanol and were collected by centrifugation (3 min, 3,500 rpm). The obtained nanoparticles were washed several times in hexane and ethanol. A diagram illustrating the synthesis scheme of the Mn-doped iron oxide nanoparticles with a central cavity is presented in FIG. 7. The results of TEM and XRD analysis of the Mn-doped iron oxide nanoparticles with a central cavity are presented in FIG. 8 and FIG. 9, respectively.

The resultant nanoparticles could be re-dispersed in chloroform, hexane or toluene for further using.

<2-2> Preparation of Mn-Doped Iron Oxide Nanoparticles with Central Cavity Using Various Manganese Oxide Nanoparticles To examine the applicability of the present invention, the preparation of Mn-doped iron oxide nanoparticles with a central cavity using various MnO nanoparticles was performed. In these experiments, Mn-doped iron oxide nanoparticles with a central cavity were prepared by the same manner as performed to prepare the Mn-doped iron oxide nanoparticles with a central cavity using octahedral MnO nanoparticles in the above, except cross-shaped, urchin-shaped or cubic MnO nanoparticles were used instead of octahedral MnO nanoparticles.

Figure 10:
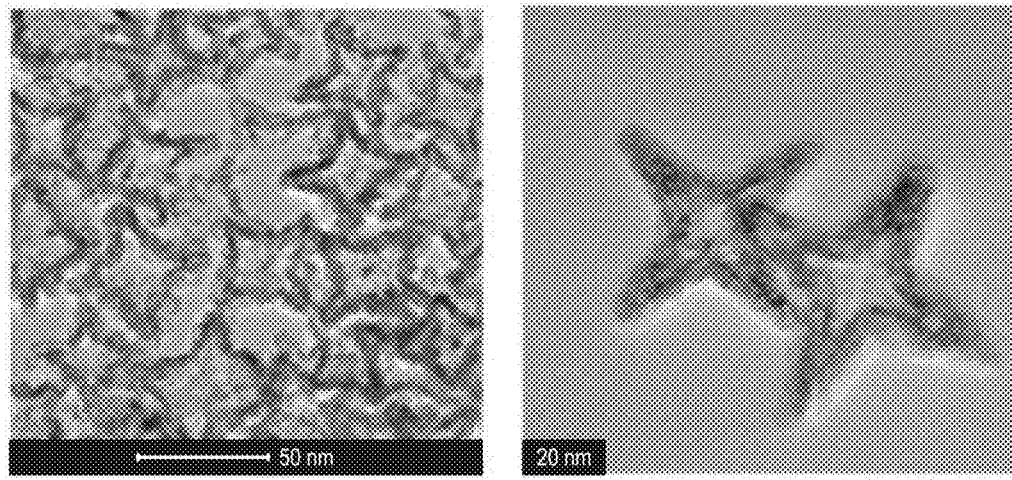
FIG. 10 is a TEM image of the Mn-doped iron oxide nanoparticles with a central cavity derived from cross-shaped MnO nanoparticles according to the present invention.
Figure 11:
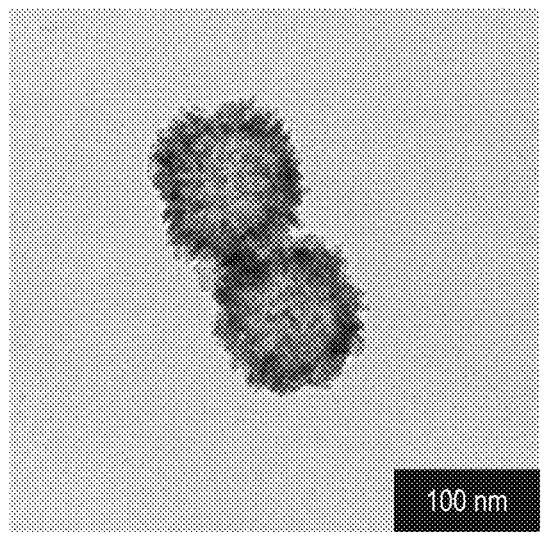
FIG. 11 is a TEM image of the Mn-doped iron oxide nanoparticles with a central cavity derived from urchin-shaped MnO nanoparticles according to the present invention.
Figure 12:
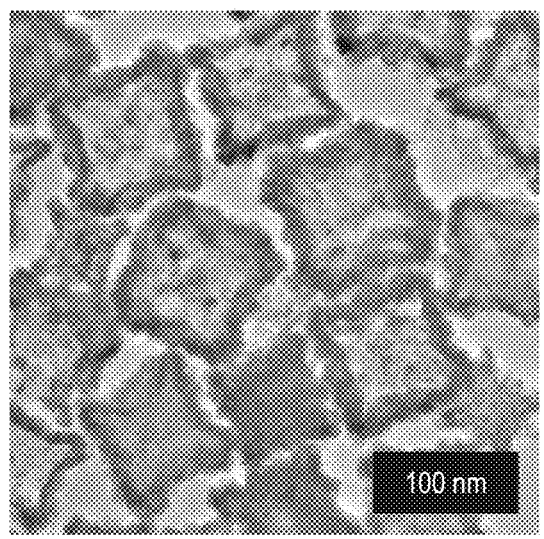
FIG. 12 is a TEM image of the Mn-doped iron oxide nanoparticles with a central cavity derived from cubic MnO nanoparticles according to the present invention.

The results of TEM analysis of the Mn-doped iron oxide nanoparticles with a central cavity are presented in FIGS. 10-12.

The resultant nanoparticles could be re-dispersed in chloroform, hexane or toluene for further using.

Example 3: Preparation of Pyrenyl Polyethylene Glycol (Pyrenyl PEG)

Pyrenyl polyethylene glycol (pyrenyl PEG) was synthesized by conjugating the amino group of hetero-functional polyethylene glycol ($NH_2$-PEGCOOH, MN: 5,000 Da) with the n-hydroxysuccinimide (NHS) group of 1-pyrenebutyric acid n-hydroxysuccinimide ester (Py-NHS, Mw: 385.41 Da). In detail, 3 mmol of Py-NHS and 1 mmol of $NH_2$-PEG-COOH were dissolved in 15 ml of dimethyl formamide, and then 200 μl of triethylamine was added to the reaction mixture at room temperature. After reacting for 48 hours at room temperature under a nitrogen atmosphere, the resultant products were filtered and washed with excess ether. The precipitates were dried under a vacuum and stored for later use.

Example 4: Loading of Drug into the Central Cavity of Mn-Doped Iron Oxide Nanoparticles Anticancer drug doxorubicin (DOX) was loaded in the central cavity of Mn-doped iron oxide nanoparticles by using typical incipient wetness method. 3 mg of DOX and 100 μl of trietylamine were dissolved in 4 ml of chloroform. Next, 10 mg of Mn-doped iron oxide nanoparticles with a central cavity dissolved in 1 ml of chloroform was added into the solution prepared above. The resultant solution was gently stirred for 10 min at room temperature and placed under vacuum to evaporate the solvent. Resultant powder was redispersed into 4 ml of chloroform and nanoparticles loaded with drug were collected with permanent magnet to remove unloaded free DOX. Above procedure was repeated three times to increase the amount DOX loaded in the nanoparticles.

Example 5: Coating of Drug-Containing Nanoparticles with Pyrenyl Polyethylene Glycol (Pyrenyl PEG)

The freshly prepared solution of Mn-doped iron oxide nanoparticles containing DOX in 1 ml of tetrahydrofuran (THF) was quickly injected into 50 ml of phosphate buffer (pH 9.8) containing 300 mg of pyrenyl PEG to minimize unwanted drug release. The resulting suspension was stirred overnight at room temperature to evaporate the organic solvent and subsequently centrifuged for 45 min at 20,000 rpm three times. After the supernatant was removed, the precipitates of DOX-containing iron oxide nanoparticles coated with pyrenyl PEG were re-dispersed in 10 ml of phosphate buffered saline (PBS; pH 7.4).

Example 6: Preparation of an MRI Contrast Agent Conjugated with Antibody

For efficient targeting, an MRI contrast agent prepared in Example 5 was conjugated with antibody. In detail, 10 µmol of 1-ethyl-3-(3-dimethylaminopropyl) carbodiimide (EDC) and 10 µmol of sulfo-n-hydroxysuccinimide (sulfo-NHS) as cross-linkers were added in 5 ml of the MRI contrast agent solution prepared in Example 5. And then, 0.7 mg (4.5 nmol) of anti HER2/neu antibody (Herceptin®; HER, Roche Pharmaceutical Ltd.) was added. The mixture was allowed to stand at 4° C. After 6 h, the MRI contrast agents conjugated with antibody (HER-conjugated MRI contrast agent) were purified by centrifugation (20,000 rpm, 45 min). Similarly, an irrelevant human immunoglobulin G (IgG) antibody (IRR) was conjugated with the MRI contrast agents by the same manner as performed to prepare the HER-conjugated MRI contrast agents in the above, except IRR was used instead of HER. The prepared IRR-conjugated MRI contrast agents were used as control MRI contrast agents without targeting molecule.

Example 7: MR Imaging 0.5 ml of HER-conjugated MRI contrast agents were administered to nude mice. And then MR imaging was performed using a 3T clinical MRI instrument with a micro-47 surface coil (Philips Medical Systems, The Netherlands). The T2-weighted MR images of nude mice injected with HER-conjugated MRI contrast agents at 3T were acquired using the following measurements at room temperature: TR=4,000 milliseconds even echo space, number of acquisitions=1, point resolution of 312×312 µm, section thickness of 0.6 mm and TE=60 msec. The results are shown in FIG. 13.

Figure 13:
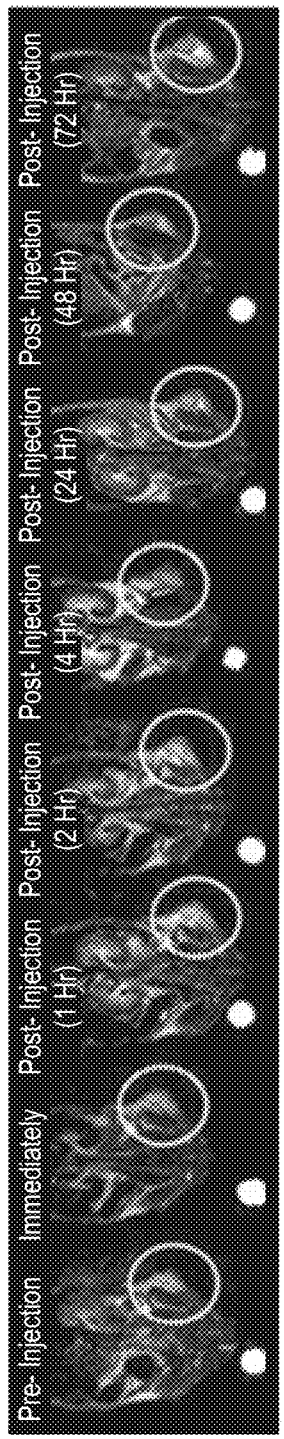
FIG. 13 is an MR image obtained using the MRI contrast agents of the present invention.

The result in FIG. 13 confirmed that the MRI contrast agent of the present invention could be used as an effective MRI contrast agent.

Example 8: Determination of the Drug Release Profile

The drug release behavior of the DOX-containing MRI contrast agents prepared according to the method of the present invention was examined under various pH conditions at 37° C.

Figure 14:
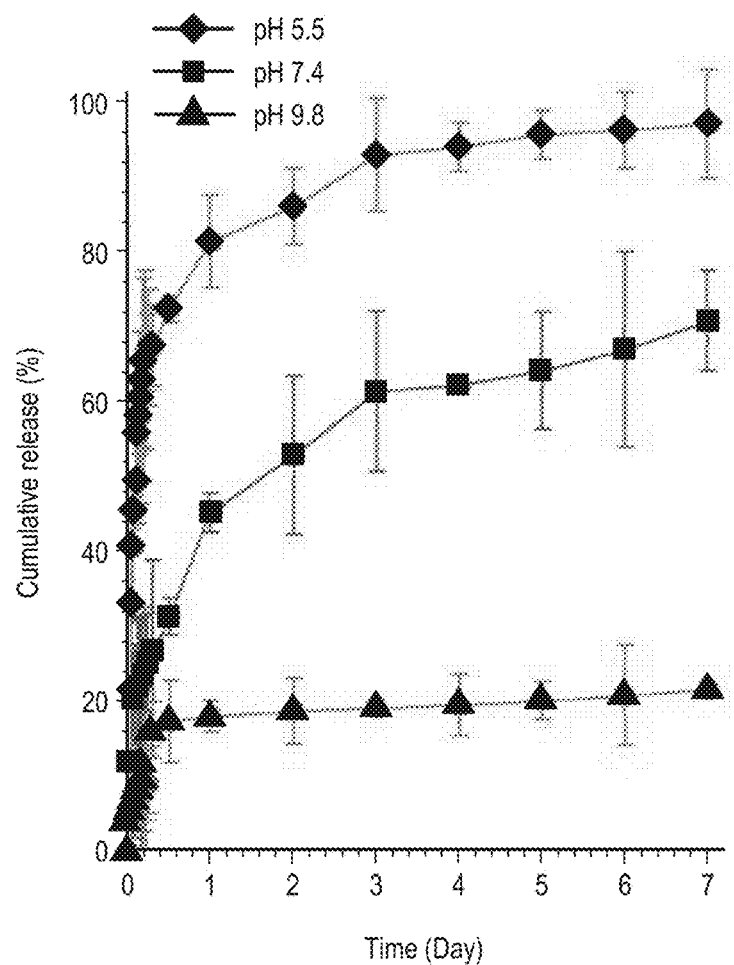
FIG. 14 a result showing the drug release profile of the MRI contrast agent of the present invention.

3 ml of the DOX-containing MRI contrast agents was centrifuged for 45 min at 20,000 rpm, and the precipitated the DOX-containing MRI contrast agents were re-dispersed in 1 ml of phosphate buffer at pH 5.5, 7.4 and 9.8, respectively. The solutions containing the DOX-containing MRI contrast agents were sealed in dialysis tubing and immersed in 10 ml of corresponding buffer solution at 37° C. The amount of released drug was measured by fluorescence at 593 nm using a fluorescence spectrometer. The results of drug release profile at various pH conditions are presented in FIG. 14. From this result, it was concluded that the efficiency of drug release was depend on the pH and the MRI contrast agent of the present invention can be used for drug delivery.

Example 9: Animal Experiment

To evaluate the effectiveness of MRI contrast agents of the present invention, the experiment using an animal model system for cancer was performed.

Figure 15:
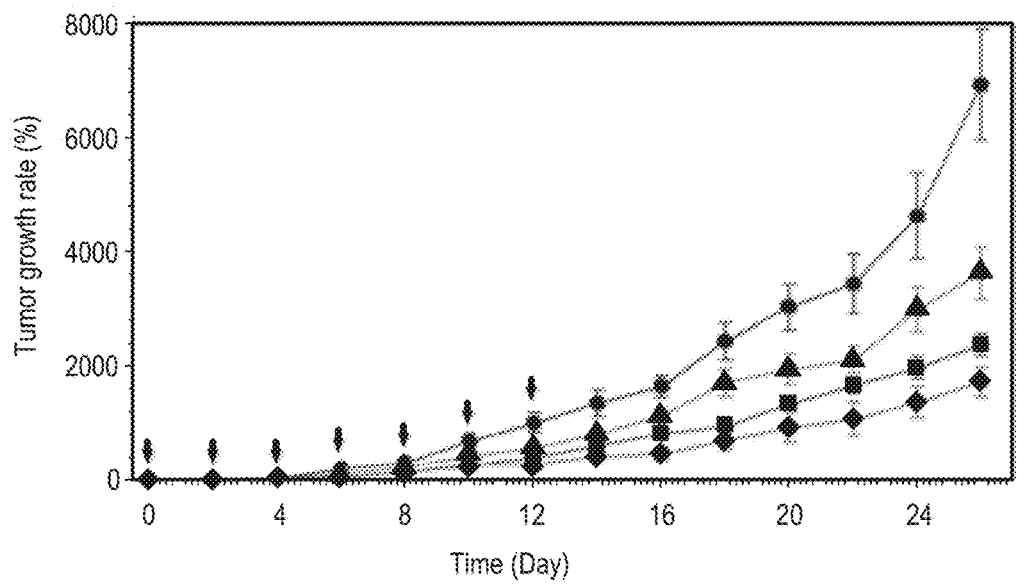
FIG. 15 is a result of animal experiment. DOX_HER: doxorubicin-containing HER-conjugated MRI contrast agents; DOX_IRR: doxorubicin-containing IRR-conjugated MRI contrast agents; DOX: doxorubicin only; and PBS: phosphate buffered saline only.

Tumor bearing mice were developed by implanting NIH3T6.7 cells ($1 \times 10^7$ cells suspended in 50 µl phosphate buffered saline) into the proximal thighs of female BALB/c nude mice that were 4-5 weeks of age. After tumor volume of the tumor bearing mice reached approximately 40 $mm^3$, at 3 days after post-implantation (day 0), MR imaging and intravenous administration of the HER-conjugated MRI contrast agent, IRR-conjugated MRI contrast agent, DOX only, or phosphate buffer only were performed. These treatments were performed every 2 days until day 12. During the rest of the experimental period (total experimental period was 26 days), only MR imaging was performed. Comparative therapeutic efficacy was evaluated by measuring the tumor volumes. The result of animal experiment is presented in FIG. 15.

Those skilled in the art will appreciate that the conceptions and specific embodiments disclosed in the foregoing description may be readily utilized as a basis for modifying or designing other embodiments for carrying out the same purposes of the present invention. Those skilled in the art will also appreciate that such equivalent embodiments do not depart from the spirit and scope of the invention as set forth in the appended claims.

The invention claimed is:

1. A method for producing a multifunctional drug delivery-MRI contrast agent derived from a porous manganese ion-doped iron oxide nanoparticle with a central cavity which is at least one of the shapes selected from the group consisting of octahedral and cross shapes, comprising the following steps:
  A) synthesizing manganese oxide nanoparticles with a central cavity which is at least one of the shapes selected from the group consisting of octahedral and cross shapes under inert gas environment;
  B) forming porous epitaxial layers of iron oxide on the surface of manganese oxide nanoparticles under inert gas environment;
  C) maintaining the formation of the layer of iron oxide under dry air environment;
  D) removing the manganese oxide by treatment with acidic liquid at high temperature to form a porous manganese ion-doped iron oxide nanoparticles having a central cavity which is at least one of the shapes selected from the group consisting of octahedral and cross shapes; and
  E) coating the nanoparticles with a biocompatible polymer.

2. The method for producing an MRI contrast agent according to claim 1, wherein the acidic liquid used in removing the manganese oxide phase is at least one selected from the group consisting of organic acids, oleic acid, palmitic acid, and acidic buffers.

3. The method for producing an MRI contrast agent according to claim 1, wherein the biocompatible polymer can be modified by conjugation with targeting moieties or diagnostic moieties.

4. The method for producing an MRI contrast agent according to claim 3, wherein the targeting moiety can be selected from the group consisting of antibodies, antibody fragment, aptamers, and various ligands binding to receptors displayed on the surface of target cell.

5. The method for producing an MRI contrast agent according to claim 3, wherein the diagnostic moiety can be selected from a group consisting of diagnostic imaging moieties which include fluorophores, optical reporters and quantum dots; computed tomography (CT) probes which include iodine-based compounds and gold nanoparticles; and nonmetallic radioisotopes selected from the group consisting of indium (In), techneticum (Tc) and fluorine (F).

6. The method for producing an MRI contrast agent according to claim 1, wherein the steps using inert gas is argon gas for synthesizing manganese oxide nanoparticles with a central cavity and for forming porous epitaxial layers of iron oxide on the surface of manganese oxide nanoparticles.

7. The method for producing an MRI contrast agent according to claim 1, wherein the nanoparticle is coated with pyrenyl polyethylene glycol.

8. The method for producing an MRI contrast agent according to claim 7, wherein the pyrenyl polyethylene glycol can be modified by conjugation with targeting moieties or diagnostic moieties.

* * * * *